United States Patent
MacLauchlan et al.

(10) Patent No.: US 6,250,163 B1
(45) Date of Patent: Jun. 26, 2001

(54) EMATS FOR SPOT WELD EXAMINATION

(75) Inventors: Daniel T. MacLauchlan, Lynchburg; Wayne M. Latham, Forest, both of VA (US)

(73) Assignee: McDermott Technology, Inc., New Orleans, LA (US)

( * ) Notice: Subject to any disclaimer, the term of this patent is extended or adjusted under 35 U.S.C. 154(b) by 0 days.

(21) Appl. No.: 09/265,436

(22) Filed: Mar. 9, 1999

(51) Int. Cl.$^7$ .................................................. G01N 29/24
(52) U.S. Cl. ................................. 73/643; 73/597; 73/599
(58) Field of Search ............................ 73/588, 643, 620, 73/624, 645, 646, 599, 600, 597; 376/252, 249

(56) References Cited

U.S. PATENT DOCUMENTS

| | | | |
|---|---|---|---|
| 2,433,963 | * 1/1948 | Tarbox et al. | 73/588 |
| 4,208,917 | * 6/1980 | Aoyama et al. | 73/644 |
| 4,265,119 | * 5/1981 | Dubetz et al. | 73/588 |
| 4,287,474 | * 9/1981 | Fastritsky et al. | 324/233 |
| 4,777,824 | * 10/1988 | Alers et al. | 73/643 |
| 5,920,014 | * 7/1999 | Waschkies | 73/597 |
| 6,072,144 | * 6/2000 | Perryman | 219/109 |

* cited by examiner

*Primary Examiner*—Hezron Williams
*Assistant Examiner*—Rose M. Miller
(74) *Attorney, Agent, or Firm*—R. J. Edwards; R. C. Baraona

(57) ABSTRACT

An EMAT apparatus which non-destructively tests spot welds between two sheets of metal. The apparatus includes a first EMAT coil on one sheet that acts as a transmitter for generating and transmitting an acoustic wave signal toward the spot weld, and a second EMAT coil on the other sheet for receiving the acoustic wave signal and converting the received acoustic wave signal to an electronic signal having a waveform. Electronics and a PC are used to measure at least one parameter of the waveform which is indicative of a characteristic of the spot weld.

24 Claims, 3 Drawing Sheets

EMAT Transducer Detail (Side View)

Permanent Magnets

EMAT Coil (Bottom View)

Transmitter EMAT        Receiver EMAT

Periodic Permanent
Magnet Arrays

EMAT Coils

EMATS FOR SPOT WELD EXAMINATION

FIELD AND BACKGROUND OF THE INVENTION

The present invention relates, in general, to devices and methods for examining welds, and in particular, to a new and useful spot weld examination apparatus and method using EMATs.

The examination of spot welds using conventional piezoelectric transducers has been established as a viable method of determining spot weld quality. The use of these transducers requires a coupling fluid or gel to be able to generate and receive ultrasonic signals. The need for a liquid couplant makes it impractical to automate this test. A large volume of background material exists for this testing. An overview of this method of testing is given in the ASNT (American Society of Nondestructive Testing) *Nondestructive Testing Handbook* Vol. 7, pages 557–568 "Ultrasonic Testing of Spot Welds in Thin Gage Steel".

Other non ultrasonic methods of spot weld testing have been publicly disclosed. The following U.S. patents are known to relate to spot weld testing:

U.S. Pat. No. 3,726,130—Method of monitoring a welding operation;

U.S. Pat. No. 4,449,092—Acoustic wave spot welder adaptive control;

U.S. Pat. No. 4,887,025—Method and apparatus for nondestructive checking of spot welds between metal sheets;

U.S. Pat. No. 5,194,709—Method for checking a spot welded portion and spot welding machine; and U.S. Pat. No. 5,399,827—Method and device for determining the temperature of a spot-welded joint and a method for assessing the quality of a spot welded joint.

In addition, a method of using Lamb waves to monitor spot welds is described in a paper "On-line Ultrasonic Lamb Wave Monitoring of Spot Welds" by S. I. Rokhlin, R. J. Mayhan and L. Adler, published in *Materials Evaluation* Vol. 43, No. 7, pages 879–883, ASNT, 1985.

At present, most spot welds used in manufacturing operations such as automotive chassis assembly are evaluated by destructively testing the welds in a statistical sampling of the assemblies. Due to economics, only a very small sampling of the assemblies are tested. If a welder develops a problem, a large number of assemblies with defective welds can be produced before the problem is detected. The manufacturer may have to scrap a large number of assemblies if a systematic problem in producing the welds is detected during destructive testing. In addition, bad welds can be produced at random, and for reasons other than welder problems. This results in assemblies that are of poorer quality that can fail prematurely in service. To compensate for the likelihood of the presence of bad welds in assemblies, the manufacturer may use a much larger number of welds than would be required if the welds were known to be good, increasing production costs. The majority of these welds receive little or no testing as to the quality of the weld.

An automated, reliable and cost effective method of nondestructively testing spot welds is needed to provide a measure of spot weld quality for each spot weld produced. The present invention satisfies that need.

An ultrasonic testing technique for nondestructive evaluation that does not need a fluid couplant has been developed within approximately the last twenty-five years. The technique depends upon electromagnetic acoustic interaction for elastic wave generation. Radio Frequency (RF) currents flowing in a flat coil placed close to a metal surface induce eddy currents in the metal surface. A static or quasi-static magnetic field is also applied to the metal surface. The eddy current flowing in the surface of the metal in the presence of the magnetic field experience a Lorentz force. This force then generates a mechanical disturbance, coupling to the atomic lattice by a scattering process. In electromagnetic acoustic generation, the electromagnetic conversion takes place directly within the eddy current skin depth. Therefore, no mechanical coupling to the body is needed. The metal surface is its own transducer. Reception takes place in a reciprocal manner.

If an elastic wave strikes the surface of the conductor in the presence of a magnetic field, induced currents are generated in the receiving coil. This is similar to the operation of an electric generator. These transducers are known as EMATs (ElectroMagnetic Acoustic Transducers). EMATs can produce a variety of wave modes including surface waves, longitudinal waves and horizontally polarized shear waves. The absence of a couplant makes it possible to design transducers that operate at elevated temperatures, can be rapidly scanned and can be easily automated. In addition, the operating characteristics of EMATs can be reproduced from one unit to another very easily.

SUMMARY OF THE INVENTION

Two concepts for employing EMATs in spot weld testing have been developed according to the present invention.

In the first approach, an EMAT is placed on a spot weld, generating and receiving shear waves that travel normal to the surface of the plates welded together. The shear wave travels through the weld to the opposite surface. It then reflects back to the surface where the transducer is positioned and is picked up by the transducer operating in a receive mode. The shear wave continues to reverberate between the two surfaces of the welded plates (top and bottom), producing signals each time it strikes the surface where the transducer is resting. If the metal plates are completely unbonded, i.e., no weld, then the shear wave reverberates between the surfaces of the plate the transducer is located on, resulting in echo spacing that is much shorter than for a good weld. If the two plates are only partially fused, then reflections from the partially disbanded areas are seen as well as reflections from the outer surface of the weld. In some cases, the spot welds fuse the two surfaces of the plates together, but the weld does not penetrate throughout the thickness of the plates resulting in a bad weld. This is known as a "cold weld" or "stick weld". In this case, large ultrasonic reverberations through the total thickness of the two plates are observed, with no reflections from the interface between the two plates, making it difficult to distinguish from the signals obtained in a good weld. However, the ultrasonic reverberations in a good weld decay more rapidly than the reverberations in a "cold" weld because a good weld produces large grains throughout the thickness of the two plates. By processing the received waveforms, the quality of the weld can be determined for the various weld conditions. As an alternative, a separate transmitter EMAT and a receiver EMAT can be used on opposite sides of the weld with similar results.

The second concept for using EMATs to test spot weld quality involves determining the time it takes for the weld to solidify after the welding current has been shut off.

Spot welding is typically used to bond two or more sheets of metal together. This is accomplished by pressing one electrode on the outer surface of the top sheet of metal and another electrode on the outside surface of the lower sheet of metal, and then passing a large current from the electrodes through the metal layers. The metal layers are heated until they become molten, fusing them together.

After the current is shut off, the metal cools and solidifies forming a spot weld. In order to test the quality of the spot welds, a pair of EMATs or ElectroMagnetic Acoustic Transducers, a transmitter EMAT and a receiver EMAT, are incorporated into the spot welder apparatus. The EMATs are connected to an EMAT pulser/receiver in the same manner as in the first concept of the invention. An N=0 Shear Horizontal (SH) plate wave is generated by the transmitter EMAT in the top layer of metal, focused through the spot weld and detected by the receiver EMAT at the bottom layer of metal. Immediately after the welder current is shut off, the transmitter EMAT is fired at a high repetition rate while monitoring the receiver EMAT.

When the metal is molten, no signal is obtained because a liquid cannot support shear waves. As soon as the weld solidifies, the shear wave is able to propagate through the weld, and a signal will be obtained at the receiver EMAT. The appearance of SH wave signals at the receiver EMAT after welding will indicate that fusion between the metal layers has taken place. By measuring the time it takes for the SH wave signal to appear after the welder current has been shut off, the time for the weld to solidify will be measured. For a known weld configuration, the measure of the time for the weld to solidify can be directly related to the total heat energy applied to the weld and is a good indicator of weld quality. In addition, by combining measurements of current, voltage, electrode pressure and the electrode movement from the welder with SH wave signal amplitude and time of appearance measurements from the EMATs, good characterization of spot weld quality can be obtained.

Accordingly, an object of the present invention is to provide an EMAT apparatus for non-destructive testing of a spot weld between two sheets of metal having inner facing surfaces, at least one of the sheets having an outer surface, the apparatus comprising: transmitter means for generating and transmitting an acoustic wave signal toward a spot weld to be tested; receiving means for receiving the acoustic wave signal and converting the received acoustic wave signal to an electronic signal having a waveform; and measuring means for measuring at least one parameter of the waveform which is indicative of a characteristic of the spot weld.

A further object of the present invention is to provide such an apparatus wherein one EMAT transducer is used both as the transmitter means and the receiver means, and is placed on the outer surface of the one sheet.

A further object of the invention is to provide such an apparatus wherein the transmitter and receiver means are two separate EMAT coils, one coil placed on the outer surface of the one sheet and the other coil placed on the outer surface of the other sheet and on opposite sides of the inner facing surfaces.

A still further object of the present invention is to measure, from the waveform, either reflections from the inner facing surfaces to indicate incomplete fusion and thus a poor spot weld, or attenuation rate of the ultrasonic reverberations, indicating a better quality weld, or the time between reverberations to determine the final weld thickness.

A still further object of the invention is to provide such an apparatus which works in conjunction with spot welding means and which operates immediately after the spot welding means is deactivated to determine the rate of solidification of the initially molten spot weld, again to indicate the quality of the weld.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

The first concept of the present invention is illustrated in FIGS. 1–4.

Figure 1:
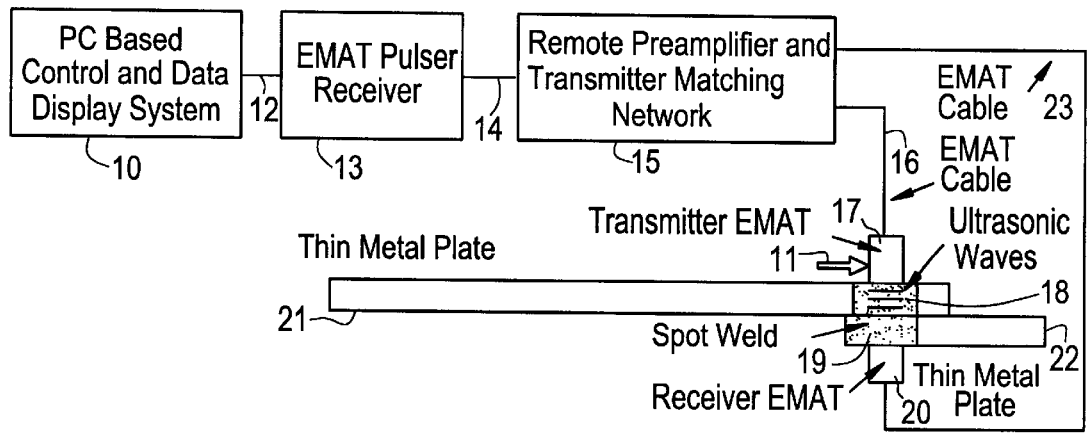
FIG. 1 is a schematic representation of a first embodiment of the present invention.

In order to investigate the use of EMATs to interrogate spot welds, a sample consisting of two 0.032" thick sheets of steel with 34 different spot welds joining them together, was obtained. The spot welds represent different quality welds and were formed by starting with very low welder current and steadily increasing the welder current for each successive weld. An EMAT system was assembled, consisting of separate transmitter and receiver EMAT operating in pitch-catch mode, as shown in FIG. 1. A standard PC equipped with a waveform digitizer card 10 was used to control an EMAT pulser/receiver 13, and to capture and display the received signals via interconnecting cables 12, as is standard practice. A single cycle 5 MHz pulse of current was sent to the remote transmitter matching network 15 via interconnecting cables 14, and on to drive the transmitter EMAT 17 via cable 16. Ultrasonic waves were launched into the spot weld 19 in two thin plates 21 and 22. The receiver EMAT 20 fed its signals into an untuned remote preamplifier 15 via cable 23. The output of the preamplifier 15 was connected to the EMAT receiver section of the EMAT pulser/receiver instrument 13 via interconnecting cables 14. The output of the receiver was sent to a waveform digitizer card in a PC 10 for recording and displaying the signals.

Figure 2:
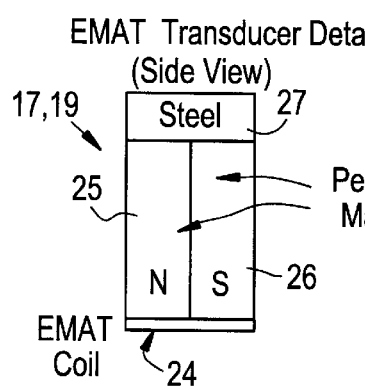
FIG. 2 is a side elevational view of an EMAT coil for use in the first embodiment.
Figure 3:
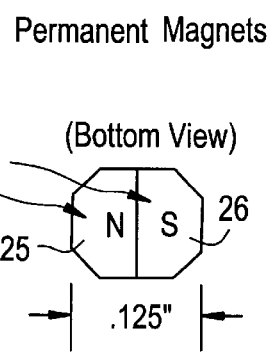
FIG. 3 is a bottom view of the EMAT coil.
Figure 4:
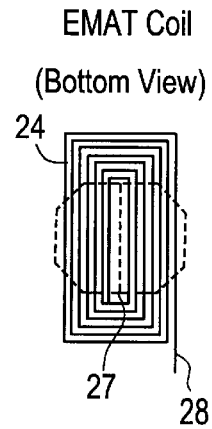
FIG. 4 is a bottom view of the conductive path forming the active coil element for the first embodiment.

The details of these EMATs are shown in FIGS. 2–4. The transmitter and receiver EMATs (17,19) were the same. The EMATs were comprised of an EMAT coil 24 and a pair of permanent magnets 25,26. A mild steel plate 27 is attached to the opposite end of the permanent magnets (25,26) from the EMAT coil 24 to serve as a low reluctance path for the magnetic flux between the ends of the magnets. The EMAT coil 24 was a flat printed circuit rectangular coil. The ends 27, 28 of EMAT coil 24 connect to the EMAT cables 16 and 23. The active areas of the EMATs 17 and 19 were approximately ⅛" by ⅛". These EMATs launch and receive ultrasonic shear waves 18, shown at FIG. 1, at normal incidence to the plate surface.

Figure 5:
FIG. 5 is an illustration of a waveform generated by the apparatus of the present invention when used to examine a good spot weld.

Using the experimental setup shown in FIGS. 1–4, waveforms from 16 of the 34 different spot welds were obtained and recorded. Weld #1 was the weld formed with the least amount of welder current and weld #34 was the weld formed with the most welder current. FIG. 5 shows the waveforms obtained from weld #19. The signals shown are the multiple reverberations through the thickness of the total weld. No reflection from the interface between the two sheets is apparent.

This represents a good weld. The pronounced exponential decay of the received signals presumably indicates attenuation of the ultrasonic signals by large grains that form in a good spot weld.

Figure 6:
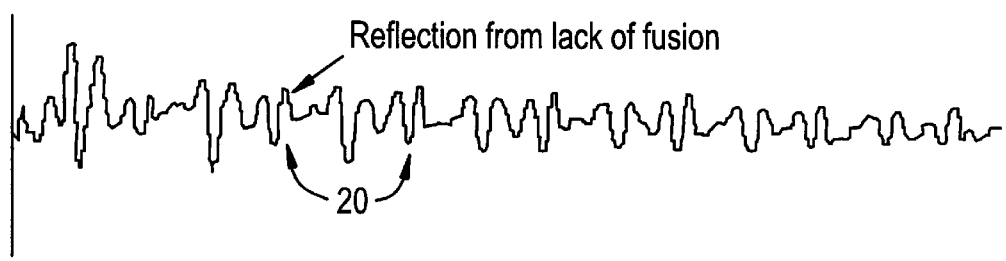
FIG. 6 is a view similar to FIG. 5 of the waveform of a poorer quality spot weld.

FIG. 6 shows the waveform obtained from the $7^{th}$ weld out of the 34. This waveform shows significant reflections 20 from the interface between the two sheets showing up in between the signals that have traveled through the full thickness of the welds. This indicates that the weld is not fully fused over the entire area of weld.

In actual on-line use, the EMAT or EMATs would be placed on the spot weld using a robotic arm or similar automated positioning device, schematically represented by arrow 11 in FIG. 1. The received signals would be digitized and processed to determine the quality of the weld. Parameters to be measured include detection of reflections from incomplete fusion between the plates, attenuation rate of the ultrasonic reverberations, and the time between reverberations to determine the final weld thickness, and to determine if the plates have been welded.

The second concept of the present invention is illustrated in FIGS. 7–10 which show a second embodiment of the present invention.

Figure 7:
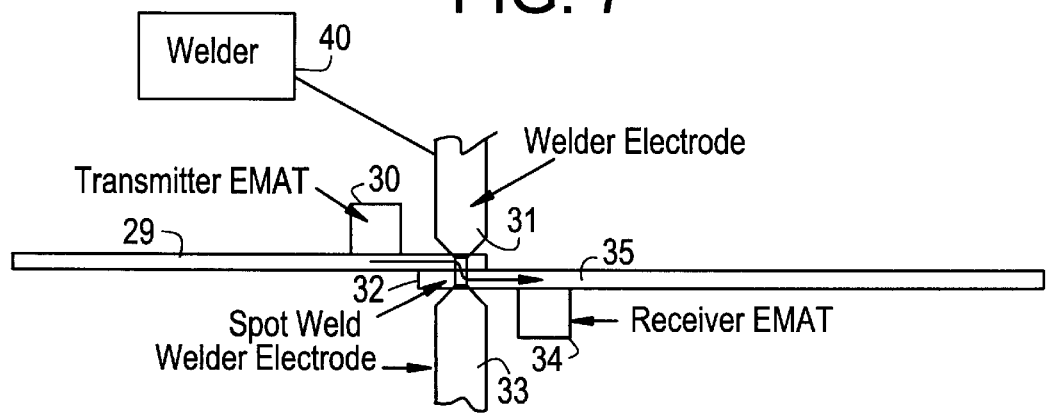
FIG. 7 is a schematic representation of a layout for a second embodiment of the present invention.

In FIG. 7, the top metal sheet 29 is spot welded at spot weld 32, formed by a spot weld device comprising a power means 40, an upper welder electrode 31 and a lower welder electrode 33. After the current between the electrodes is turned off, the quality of spot weld 32 is determined using a transmitter EMAT 30 and a receiver EMAT 34 positioned respectively on the top of first metal sheet 29 and the bottom of second metal sheet 35. Electronic powering and retrieval of signals to and from the EMATs uses the same equipment shown, for example, in FIG. 1. A shear horizontal (SH) plate wave shown at 40 in FIG. 8 where N=0, is generated by energizing transmitter EMAT 30. This wave is focused through spot weld 32 and the wave is detected by receiver EMAT 34. Immediately after the weld current is shut off, the transmitter EMAT fires at high repetition rate while monitoring the receiver EMAT. Shear waves cannot be supported when the weld is molten, but as soon as the weld solidifies, signals are received. The extent of fusion of the two sheets will be apparent in the received waveform by measuring the time it takes the SH wave signal to appear after the welder current has been turned off. This indicates the time it took the weld to solidify. This time is directly related to the total heat energy applied to the weld and is a good indication of weld quality. This signal can be combined with measurements for current, voltage, electrode pressure and electrode movement from the welder, as well as the amplitude and time of appearance of the SH wave signal, to fully characterize the quality of spot weld 32.

Figure 8:
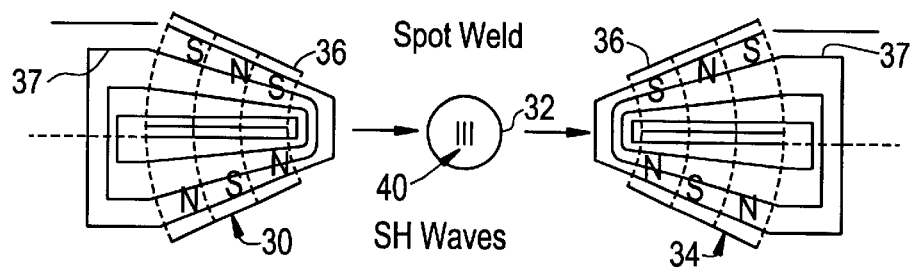
FIG. 8 is a bottom view of the magnet arrays for the coils of the second embodiment.
Figure 9:
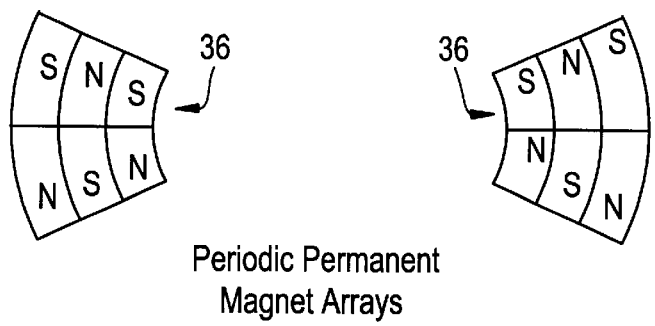
FIG. 9 illustrates the magnet array alone without the coils.
Figure 10:
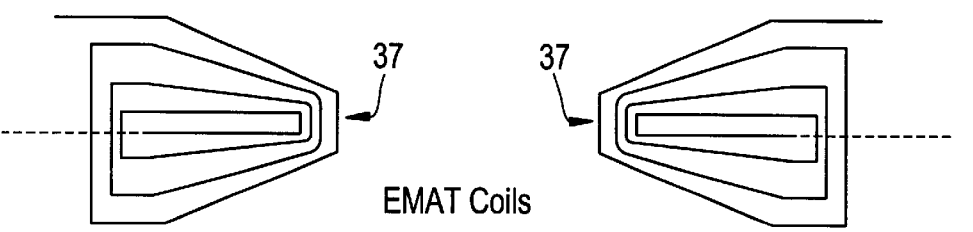
FIG. 10 illustrates the coils without the magnet array.

FIG. 8 is a bottom view of the permanent magnet arrays 36 and coils 37 that comprise the EMATs 30 and 34. The magnetic arrays and coils are the same for both the transmitter and receiver. By using circular arc segments in the magnet array 26 (see FIG. 9 as well), the SH waves can be focused through the center of the spot weld. The N=0 SH plate wave can be generated using such transducers independent of the plate thickness, allowing one probe set to cover a wide range of plate thickness. FIG. 10 shows the coils 37 above.

The first concept of the invention illustrated in FIGS. 1–6 is very similar to spot weld testing developed using conventional ultrasonic testing. The use of EMATs eliminates the need to supply a couplant between the transducer and the weld surface. This allows the test to be much more readily automated, eliminating the need to apply the couplant to the weld surface and remove the couplant after testing. In addition, EMATs can operate at elevated temperatures, allowing the welds to be tested shortly after welding, reducing the feedback loop for quality control of the welding process.

The second concept of FIGS. 7–10 is unique to EMATs in that it is impractical to generate SH waves using conventional ultrasonics. This approach has several significant advantages for spot weld testing. The EMAT probes could be part of the welder assembly, it would not require separate positioning mechanics and time to position the probes. The evaluation of the weld would be made as soon as the weld solidifies, resulting in the ability to immediately feedback information on the quality of the weld so that corrections to the welding process could be made if needed before even one more weld is made. Since EMATs are able to operate at elevated temperatures, the transducers would not be affected by the heating caused by the welding process. The use of the N=0 SH wave mode allows the same probes to be used over a range of plate thickness.

For the first concept, other EMAT configurations for generating a normal beam ultrasonic wave are possible including the use of a single permanent magnet with either a spiral coil or section of a rectangular coil under it. Also, an electromagnet or pulsed electromagnet could be used to generate the needed magnetic field.

For the second concept, other configurations for arrangement of the EMAT coil and periodic magnet array are possible to generate the SH waves. The SH waves could also be generated using magnetostriction and a meander coil EMAT with curved wires to focus the ultrasound.

While a specific embodiment of the invention has been shown and described in detail to illustrate the application of the principles of the invention, it will be understood that the invention may be embodied otherwise without departing from such principles.

What is claimed is:

1. An EMAT apparatus for non-destructive testing of a spot weld between two sheets of metal having inner facing surfaces, at least one of the sheets having an outer surface, the apparatus comprising:

transmitter means for generating and transmitting an acoustic wave signal toward a spot weld to be tested;

receiving means for receiving the acoustic wave signal and converting the received acoustic wave signal to an electronic signal having a waveform; and measuring means for measuring at least one parameter of the waveform which is indicative of a characteristic of the spot weld.

2. An EMAT apparatus according to claim 1, wherein the transmitter means comprises an EMAT transmitter on the outer surface of the one sheet of metal and the receiving means comprises an EMAT receiver on an outer surface of the other sheet of metal, opposite from the inner facing surfaces.

3. An EMAT apparatus according to claim 1, wherein the transmitter and receiver means comprise a single EMAT coil on the outer surface of the one sheet which acts as the transmitter means during part of its period of operation and as the receiving means during another part of its operation.

4. An EMAT apparatus according to claim 1, wherein the waveform includes reverberations and reflections, the parameter to be measured by the measuring means comprising at least one of: reflections at the inner facing surfaces indicating incomplete fusion of the spot weld; attenuation rate of the reverberations; and time between reverberations.

5. An EMAT apparatus according to claim 1, wherein at least one of the transmitter and receiving means comprises an EMAT coil having a pair of permanent magnets with opposite poles at one end of the EMAT coil and a mild steel plate at an opposite end of the permanent magnets, the EMAT coil having a coil pattern at the first end thereof.

6. An EMAT apparatus according to claim 2, wherein the EMAT transmitter and the EMAT receiver both comprise curved pairs of permanent magnets with a curvature having a center substantially at a spot weld to be tested at the inner facing surfaces of the two sheets of metal.

7. An EMAT apparatus according to claim 1, including welding means for forming a spot weld at the inner facing surfaces and power means connected to the weld means for powering the weld means, the transmitter and receiving means being operatively connected to the power means for generating and transmitting the acoustic wave shortly after the power means is deactivated.

8. An EMAT apparatus according to claim 7, wherein the at least one parameter measured by the measuring means comprises a period of time between deactivation of the power means and occurrence of an initial acoustic wave signal in the waveform which indicates solidification of the initially molten metal forming the spot weld.

9. An EMAT apparatus according to claim 8, including second measuring means connected to the power means for measuring at least one parameter of the power means in conjunction with the measuring means for measuring the at least one parameter of the waveform for indicating a characteristic of the spot weld.

10. An EMAT method for non-destructive testing of a spot weld between two sheets of metal having inner facing surfaces, at least one of the sheets having an outer surface, the apparatus comprising:

generating and transmitting an acoustic wave signal toward a spot weld to be tested;

receiving the acoustic wave signal and converting the received acoustic wave signal to an electronic signal having a waveform; and measuring at least one parameter of the waveform which is indicative of a characteristic of the spot weld.

11. The EMAT method according to claim 10, wherein an EMAT transmitter is on the outer surface of the one sheet of metal and an EMAT receiver is on an outer surface of the other sheet of metal, opposite from the inner facing surfaces.

12. The EMAT method according to claim 11, wherein the EMAT transmitter and the EMAT receiver each comprise a single EMAT coil on the outer surface of the one sheet of metal which acts as the EMAT transmitter means during part of its period of operation and as the EMAT receiver during another part of its operation.

13. The EMAT method according to claim 10, wherein the parameter to be measured by the measuring step comprising at least one of: reflections at the inner facing surfaces indicating incomplete fusion of the spot weld; attenuation rate of the reverberations; and time between reverberations.

14. The EMAT method according to claim 11, wherein the EMAT transmitter and the EMAT receiver each comprise an EMAT coil having a pair of permanent magnets with opposite poles at one end of the EMAT coil and a mild steel plate at an opposite end of the permanent magnets, the EMAT coil having a coil pattern at the first end thereof.

15. The EMAT method according to claim 11, wherein the EMAT transmitter and the EMAT receiver each comprise curved pairs of permanent magnets with a curvature having a center substantially at the spot weld to be tested at the inner facing surfaces of the two sheets of metal.

16. The EMAT method according to claim 10, including:

welding the spot weld at the inner facing surfaces, the welding powered by a power means; and deactivating the power means prior to the step of generating and transmitting the acoustic wave signal.

17. The EMAT method according to claim 16, wherein the at least one parameter measured by the measuring step comprises a period of time between deactivation of the power means and occurrence of an initial acoustic wave signal in the waveform which indicates solidification of the initially molten metal forming the spot weld.

18. An EMAT method according to claim 16, further comprising:

measuring at least one parameter of the power means in conjunction with the step of measuring the at least one parameter of the waveform for indicating a characteristic of the spot weld.

19. An EMAT apparatus for non-destructive testing of a spot weld between two sheets of metal having inner facing surfaces, at least one of the sheets having an outer surface, the apparatus comprising:

an EMAT transmitter on the outer surface of the one sheet of metal;

an EMAT receiver on an outer surface of the other sheet of metal, opposite from the inner facing surfaces, the EMAT transmitter and the EMAT receiver each comprising curved pairs of permanent magnets with a curvature having a center substantially at the spot weld; and measuring means for measuring at least one parameter of the waveform which is indicative of a characteristic of the spot weld.

20. An EMAT apparatus for non-destructive testing of a spot weld between two sheets of metal having inner facing surfaces, at least one of the sheets having an outer surface, the apparatus comprising:

transmitter means for generating and transmitting an acoustic wave signal toward a spot weld to be tested;

receiving means for receiving the acoustic wave signal and converting the received acoustic wave signal to an electronic signal having a waveform;

welding means for forming a spot weld at the inner facing surfaces;

power means connected to the welding means for powering the welding means, the transmitter and receiving means being operatively connected to the power means for generating and transmitting the acoustic wave shortly after the power means is deactivated; and measuring means for measuring at least one parameter of the waveform which is indicative of a characteristic of the spot weld, wherein the at least one parameter comprising a period of time between deactivation of the power means and occurrence of an initial acoustic wave signal in the waveform which indicates solidification of the initially molten metal forming the spot weld.

21. An EMAT apparatus according to claim 20, further comprising:

second measuring means connected to the power means for measuring at least one parameter of the power means in conjunction with the measuring means for measuring the at least one parameter of the waveform for indicating a characteristic of the spot weld.

22. An EMAT method for non-destructive testing of a spot weld between two sheets of metal having inner facing surfaces, at least one of the sheets having an outer surface, wherein an EMAT transmitter is on the outer surface of the one sheet of metal and an EMAT receiver is on an outer surface of the other sheet of metal, opposite from the inner facing surfaces, the EMAT transmitter and the EMAT receiver each comprising curved pairs of permanent magnets with a curvature having a center substantially at a spot weld, the method comprising:

generating and transmitting an acoustic wave signal toward a spot weld to be tested;

receiving the acoustic wave signal and converting the received acoustic wave signal to an electronic signal having a waveform; and measuring at least one parameter of the waveform which is indicative of a characteristic of the spot weld.

23. An EMAT method for non-destructive testing of a spot weld between two sheets of metal having inner facing surfaces, at least one of the sheets having an outer surface, the apparatus comprising:

welding the spot weld at the inner facing surfaces, the welding powered by a power means;

deactivating the power means;

generating and transmitting an acoustic wave signal toward the spot weld to be tested;

receiving the acoustic wave signal and converting the received acoustic wave signal to an electronic signal having a waveform;

measuring at least one parameter of the waveform which is indicative of a characteristic of the spot weld, the at least one parameter of the waveform comprising a period of time between deactivation of the power means and occurrence of an initial acoustic wave signal in the waveform which indicates solidification of the initially molten metal forming the spot weld.

24. An EMAT method according to claim 23 further comprising:

measuring at least one parameter of the power means in conjunction with the measuring the at least one parameter of the waveform for indicating a characteristic of the spot weld.

* * * * *